United States Patent
Zhu et al.

[11] Patent Number: 5,927,351
[45] Date of Patent: Jul. 27, 1999

[54] DRAWING STATION SYSTEM FOR RADIOACTIVE MATERIAL

[75] Inventors: Bing Bing Zhu, Northridge; Monty Mong Chen Fu, Canyon Country; Richard L. Green, Simi Valley; Haig S. Bagerdjian, Reseda, all of Calif.

[73] Assignee: Syncor International Corp., Woodland Hills, Calif.

[21] Appl. No.: 08/866,733

[22] Filed: May 30, 1997

[51] Int. Cl.$^6$ .................................................. B65B 1/04
[52] U.S. Cl. ............................................ 141/330; 141/329
[58] Field of Search ................................... 141/330, 329, 141/19, 27, 26, 25, 23, 21; 248/333, 130, 131, 132, 133, 139, 142, 416, 419, 179.1, 183.1; 250/453.11, 522.1, 507.1, 506.1; 220/230, 256; 206/365; 600/4, 5; 604/201, 199; 222/160, 164, 165, 167, 168

[56] References Cited

U.S. PATENT DOCUMENTS

| | | |
|---|---|---|
| D. 208,080 | 7/1967 | Hamilton . |
| D. 324,101 | 2/1992 | Reif et al. . |
| D. 333,347 | 2/1993 | Kemp et al. . |
| 2,682,652 | 6/1954 | Hawkins et al. . |
| 2,812,231 | 11/1957 | Zar . |
| 3,074,542 | 1/1963 | Myerson et al. . |
| 3,101,841 | 8/1963 | Baldwin . |
| 3,149,717 | 9/1964 | Castelli . |
| 3,272,322 | 9/1966 | Ogle . |
| 3,294,231 | 12/1966 | Vanderbeck . |
| 3,329,146 | 7/1967 | Waldman, Jr. . |
| 3,344,787 | 10/1967 | MacLean . |
| 3,367,488 | 2/1968 | Hamilton . |
| 3,531,644 | 9/1970 | Koster . |
| 3,673,411 | 6/1972 | Glasser . |
| 3,677,247 | 7/1972 | Brown . |
| 3,731,100 | 5/1973 | Lattin . |
| 3,882,315 | 5/1975 | Soldan . |
| 3,971,955 | 7/1976 | Heyer et al. . |
| 4,062,353 | 12/1977 | Foster et al. . |
| 4,081,688 | 3/1978 | Fries . |
| 4,106,622 | 8/1978 | Windischman . |
| 4,113,090 | 9/1978 | Carstens . |
| 4,122,836 | 10/1979 | Burnett . |
| 4,223,799 | 9/1980 | Eyster et al. ............................ 220/230 |
| 4,307,713 | 12/1981 | Galkin et al. . |
| 4,357,541 | 11/1982 | Ernst . |
| 4,382,512 | 5/1983 | Furminger . |
| 4,393,864 | 7/1983 | Galkin et al. . |
| 4,401,108 | 8/1983 | Galkin et al. . |
| 4,671,477 | 6/1987 | Cullen .................................... 248/122 |
| 4,745,907 | 5/1988 | Russel, Jr. et al. . |
| 4,781,697 | 11/1988 | Slaughter . |

(List continued on next page.)

OTHER PUBLICATIONS

Advertisement: May 1996, "The Solution To A Broken Syringe Is As Easy As 1–2–3," by Capintec, Inc.
Advertisement for "Syringe Shields".
Advertisement for "Pro–Tec III® Syringe Shield".
Advertisement for "Pro–Tec II® Syringe Shield".
Advertisement for Pro–Tec β Syringe Shield.
Advertisement for Pro–Tec® Syringe Shield.
Synor Corporation Brochure "Introducing The Secure™ Safety Injection Shield Another Safety First!".

*Primary Examiner*—David J. Walczak
*Attorney, Agent, or Firm*—Keith A. Newburry, Esq.; Sheppard, Mullin, Richter & Hampton LLP

[57] ABSTRACT

An improved drawing station system for handling radioactive material for use in syringes in the health care industry. The system includes a drawing station, a syringe shield and two different radiopharmaceutical pigs. The drawing station has a base with a support and two arms mounted thereto to support a first radiopharmaceutical pig enclosing a container of radioactive material. The radiopharmaceutical pig is releasably mounted to the second arm so that the radiopharmaceutical pig is pivotable about two predetermined axes to position the container for penetration by the syringe needle to draw radioactive material from the container into the syringe.

33 Claims, 7 Drawing Sheets

U.S. PATENT DOCUMENTS

| | | |
|---|---|---|
| 4,846,235 | 7/1989 | Handke . |
| 4,851,702 | 7/1989 | Perlman . |
| 4,869,299 | 9/1989 | Handke . |
| 4,892,525 | 1/1990 | Hermann, Jr. et al. . |
| 4,917,263 | 4/1990 | Korb . |
| 5,042,679 | 8/1991 | Crowson et al. . |
| 5,066,597 | 11/1991 | Stinson et al. . |
| 5,096,062 | 3/1992 | Burkardt et al. . |
| 5,099,998 | 3/1992 | Curzon et al. . |
| 5,145,063 | 9/1992 | Lee . |
| 5,157,900 | 10/1992 | Kupersmit . |
| 5,205,408 | 4/1993 | Cobb . |
| 5,245,117 | 9/1993 | Withers et al. . |
| 5,274,239 | 12/1993 | Lane et al. . |
| 5,277,312 | 1/1994 | Vumbaca . |
| 5,303,836 | 4/1994 | Childress . |
| 5,323,719 | 6/1994 | Withers et al. . |
| 5,385,105 | 1/1995 | Withers, Jr. et al. . |
| 5,397,902 | 3/1995 | Castner et al. . |
| 5,417,326 | 5/1995 | Winer . |
| 5,519,931 | 5/1996 | Reich . |
| 5,536,945 | 7/1996 | Reich . |
| 5,552,612 | 9/1996 | Katayama et al. . |
| 5,672,883 | 9/1997 | Reich . |

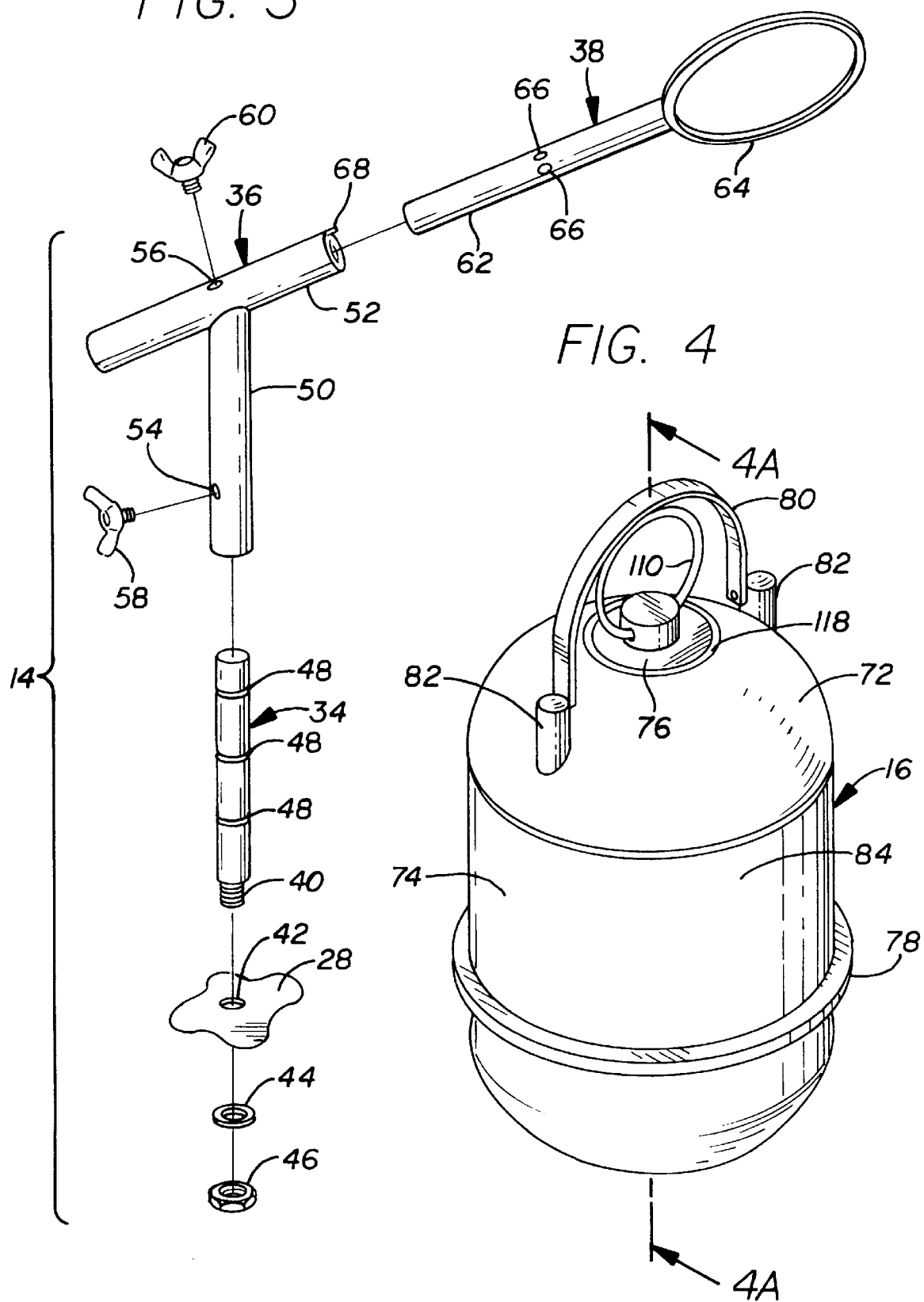

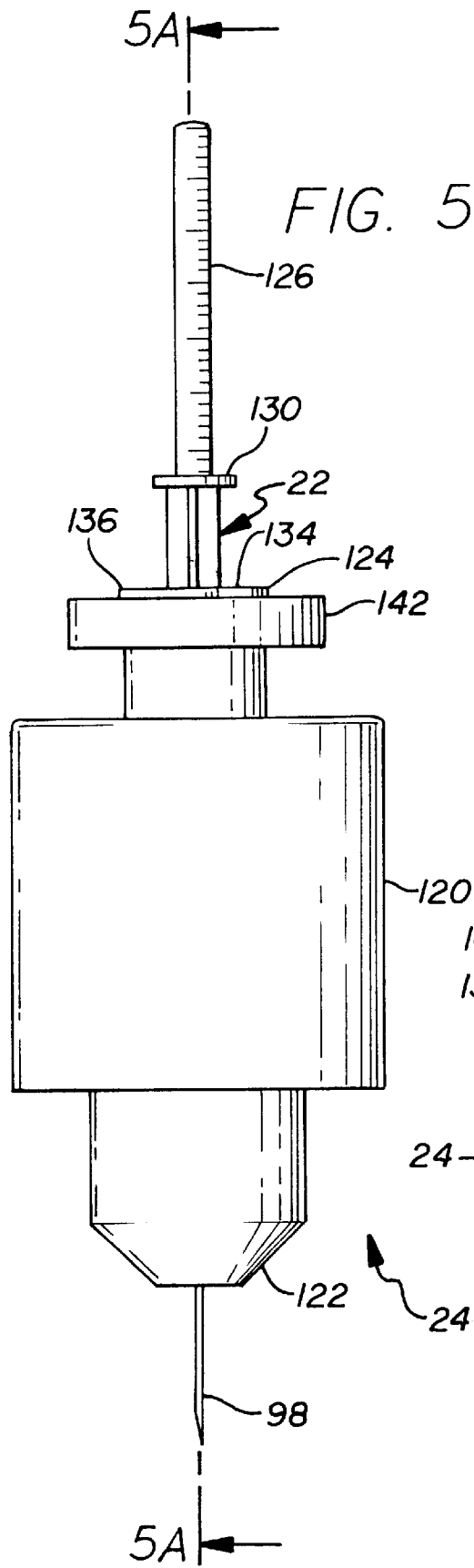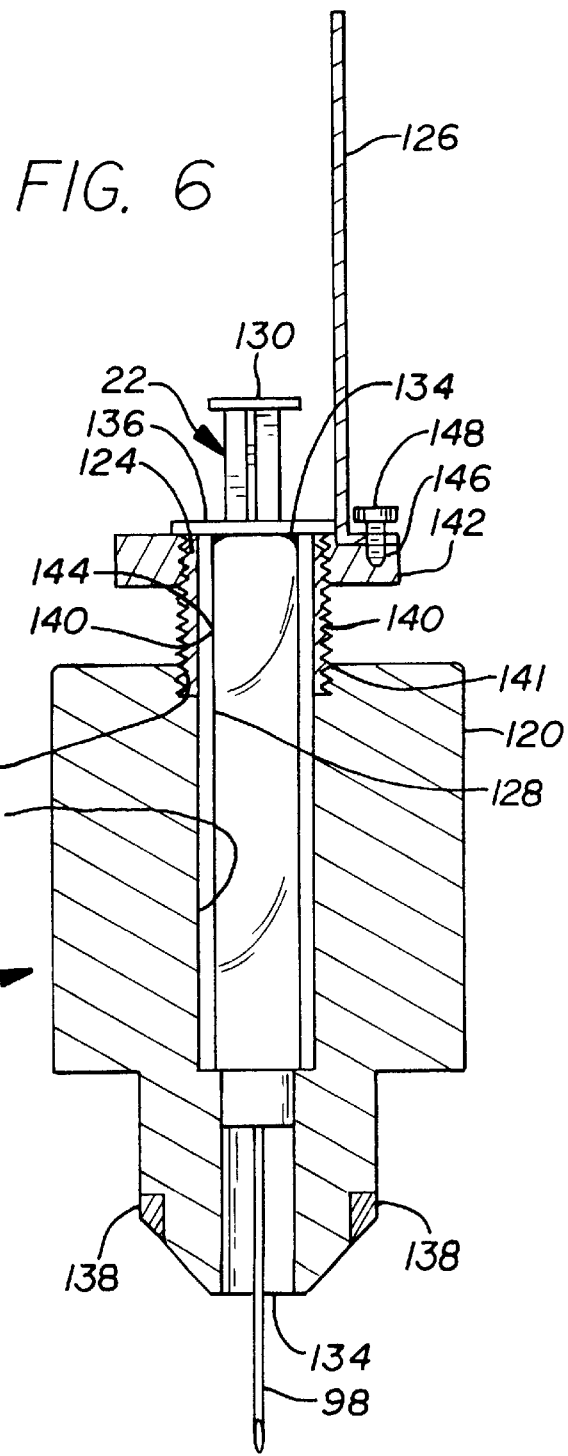

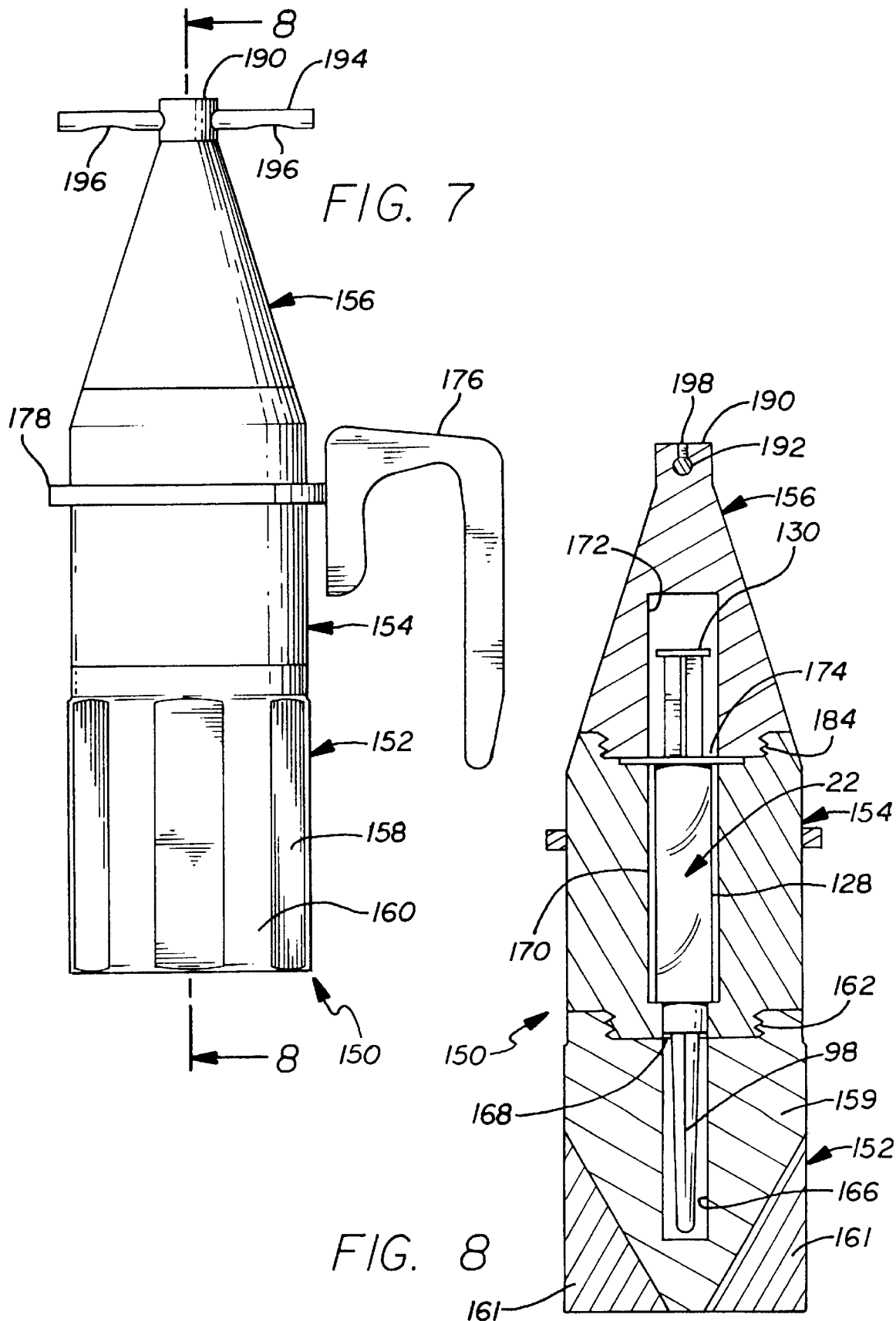

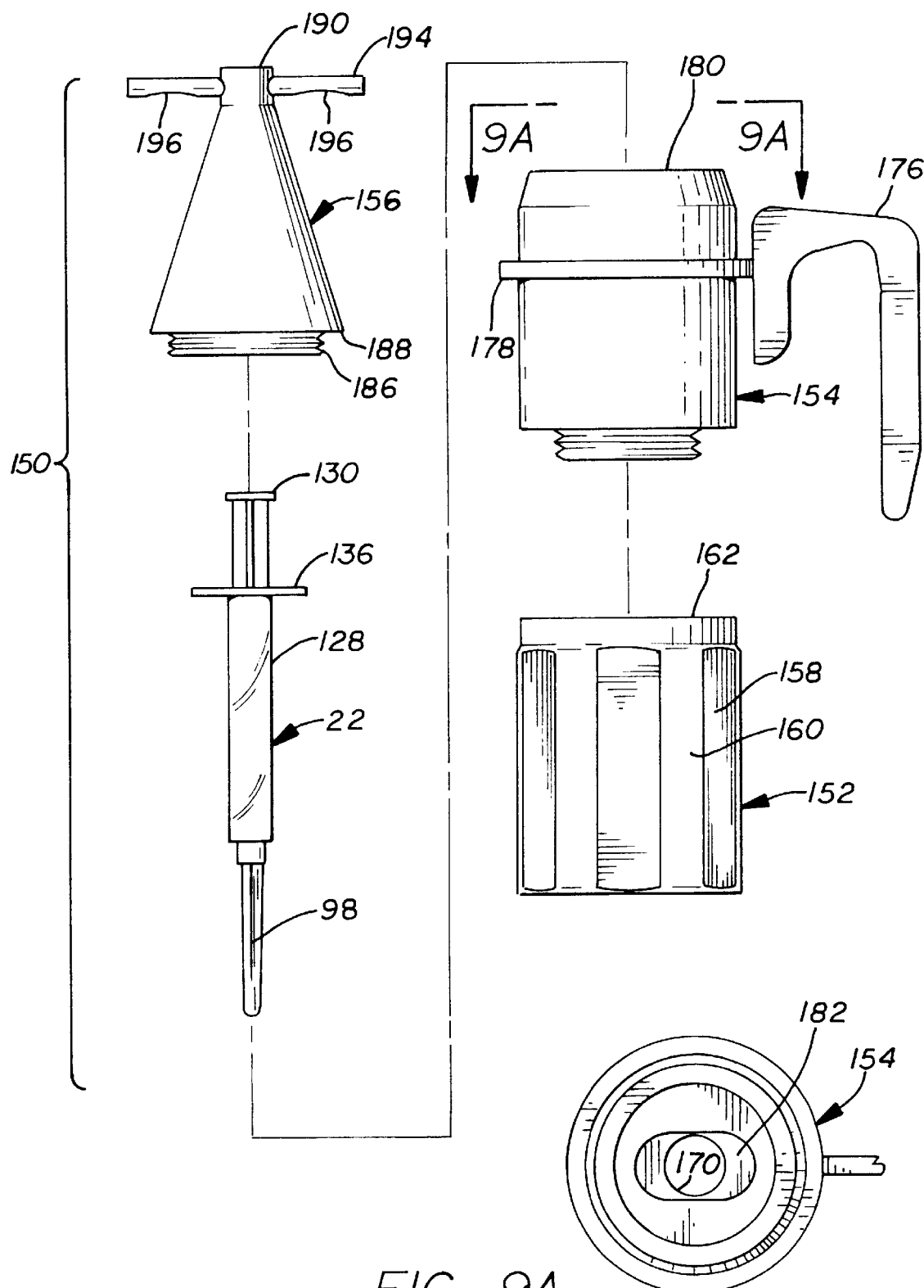

DRAWING STATION SYSTEM FOR RADIOACTIVE MATERIAL

BACKGROUND OF THE INVENTION

The present invention generally relates to shielded containers for the handling of radioactive materials and, more particularly, to radiation-resistant shields allowing improved handling of radioactive materials used in the health care industry.

In the health care industry and more specifically in the filed of nuclear medicine, radioactive materials known as radiopharmaceuticals are used in various applications, including non-intrusive imaging of patients for various diagnostic as well as therapeutic purposes. Over the years, the health care industry has developed many different radiopharmaceuticals designed to facilitate such applications. Radiopharmaceuticals are generally used in a liquid form suitable for injection into a patient via standard 3 cc or 5 cc hypodermic syringes.

Because of the radioactive nature of radiopharmaceuticals, they should be handled carefully and various governmental agencies, including the U.S. Department of Transportation, the Nuclear Regulatory Commission, and the Occupational Health and Safety Administration have promulgated regulations for safe handling of such materials. In addition to the radioactivity of the radiopharmaceutical, the biologically contaminated needle of the used syringe can pose a risk to disposal workers. To avoid some of the overhead costs associated with addressing the above concerns, many hospitals have resorted to outside pharmacy companies having expertise in the compounding and handling of radiopharmaceuticals.

Typically, health care providers order radiopharmaceuticals in syringes containing an individual dose for a specific patient. Methods and apparatus for safe handling of syringes containing conventional radiopharmaceuticals have been developed. For example, a system for transporting syringes containing radiopharmaceuticals is disclosed in U.S. Pat. Nos. 5,519,931 and 5,536,945.

One type of imaging process that has received increasing attention in the health care industry is known as positron emission tomography ("PET"). In general, the PET process involves the use of a radiopharmaceutical labeled with a positron-emitting isotope, administered intravenously to a patient. Cyclotron machines are used to produce PET isotopes, which can be highly radioactive. After injection of the PET radiopharmaceutical, a PET scanner can image the distribution of the PET radiopharmaceutical in the area of interest within the patient's body. As is well known, the PET imaging process can yield superior results as compared to conventional nuclear medicine imaging techniques.

Because PET radiopharmaceuticals can be much more radioactive than conventional radiopharmaceuticals, conventional handling techniques are not well suited for the effective transport and handling of PET radiopharmaceuticals. To address this problem, transportation containers with massive lead shields have been used as transport containers. These heavy containers, weighing well over 100 pounds, are not easily moved and handled, thereby making compounding and delivery of PET radiopharmaceuticals extremely difficult from a logistical standpoint. For example, because PET radiopharmaceuticals have very short half lives, some on the order of 20 minutes, the use of massive lead shields and massive transportation containers does not facilitate the quick handling required to distribute these radiopharmaceuticals before they decay.

Another drawback is related to the handling of the PET isotopes and radiopharmaceuticals during compounding. In particular, pharmacists use what is known as a "drawing station" to fill a syringe from a standard septum-topped vial containing PET radiopharmaceutical or PET isotope. One conventional drawing station has a massive lead shield that is pivotally mounted between opposing arms projecting upwardly from a base. The vial is delivered to the drawing station in a small tungsten insert that is placed into a cavity in the lead shield, which, by manually turning a crank, can be rotated to hold the vial in an inverted position. Once in the inverted position, a syringe needle can be inserted upward through the septum of the vial and the syringe can draw the PET radiopharmaceutical from the vial. The syringe is held within a shield that twists onto the drawing station to shield the syringe during the drawing process.

While the PET drawing station described above has been generally satisfactory, it has many drawbacks. For example, the lead shield is very massive and it is difficult for health care workers to rotate it during the drawing process. Another drawback is related to the tungsten insert, which does not shield radiation as well as the lead shield into which it is inserted. Thus, during the time that the insert is not within the massive lead shield, more radiation is emitted from the insert than would escape from the lead shield. Another drawback is that the insert exposes the vial during the drawing process, thereby allowing unwanted radiation exposure.

Yet another drawback is related to the twist-on mounting mechanism that allows the syringe shield to be joined with the drawing station. During the time required for health care workers to align the twist-on mechanism on the syringe shield with its corresponding receiving structure on the drawing station, unwanted radiation exposure can occur. Further, if the alignment process takes more than a few minutes, the PET isotope will have lost a significant amount of radioactivity due to the PET isotope's short half life.

After the drawing process is completed, the syringe containing the PET radiopharmaceutical is delivered to the patient for injection. One conventional radiopharmaceutical transportation container has a twist-on cap that mates with a housing to hold a syringe therein. While this container is generally acceptable for less radioactive radiopharmaceuticals, it has certain drawbacks when used with highly radioactive PET radiopharmaceuticals. One such drawback is that this transportation container permits radiation exposure when the container is opened to allow access to the syringe held therein. Yet another drawback is associated with the mechanism that is used to hold the cap to the housing. In particular, there is radiation exposure from the container during the time required to screw the cap to the housing.

Accordingly, there exists a need for an improved drawing station system for handling radioactive materials used in compound nuclear medicines. The present invention satisfies this need and provides further related advantages.

SUMMARY OF THE INVENTION

Briefly, and in general terms, the present invention resides in an improved drawing station system for handling radioactive materials for use in compounding nuclear medicines. The system also has a number of significant related advantages.

As will be described below, the drawing station system advantageously allows a health care worker to easily pivot a radiopharmaceutical pig about two axes to position the radiopharmaceutical pig for a transfer of the radioactive material from the radiopharmaceutical pig to a syringe. Further, as also will be described below, the radiopharmaceutical pig has a magnetically mounted cap that can be removed and replaced very quickly, thereby advantageously reducing the wasted time in which the radioactive material decays.

More specifically, and by way of example only, the drawing system is used for transferring radioactive material from a container of radioactive material to a syringe. In one embodiment, the syringe has a tubular body with a needle protruding from one end of its body and a plunger protruding from the other. The system includes a base with a support and two arms mounted thereto to support a radiopharmaceutical pig. The support extends upwardly from the base and the first arm is pivotally mounted to the support for rotation about a first predetermined axis. The second arm is pivotally mounted to the first arm for rotation about a second predetermined axis. The radiopharmaceutical pig has a cap and an interior surface defining a cavity with an opening sized to accept the cap to thereby enclose the container of radioactive material in the cavity. The opening is positioned adjacent to the container to allow access thereto. The radiopharmaceutical pig is releasably mounted to the second arm so that the radiopharmaceutical pig is pivotable about both predetermined axes to position the container for penetration by the syringe needle to draw radioactive material from the container into the syringe.

In another embodiment of the invention, a syringe shield is provided that has a proximal end, a distal end and an interior surface extending therebetween to define a passage with openings in each end of the shield. The passage is sized to accept the syringe therein, with the needle of the syringe projecting from the proximal end of the shield. The proximal end of the shield is configured to mate with the opening in the radiopharmaceutical pig to shield the opening of the pig after the needle has been inserted into the container.

In a more detailed aspect of this embodiment of the invention, the shield has a volume scale located adjacent to its distal end. The scale is marked so that the amount of material in the syringe can be determined without the need to view the body of the syringe. The volume of the syringe can be determined by simply observing the change in position of the end of the syringe's plunger. If the shield is used for highly radioactive material, such as PET radiopharmaceuticals and isotopes, the syringe shield does not have a window for viewing the volume of the material in the body of the syringe.

In another embodiment of the invention, the cap of the radiopharmaceutical pig is magnetically mounted to the body of the pig. This advantageously allows the quick removal and replacement of the cap, thereby reducing radiation exposure and wasted time in which the material degrades due to its half-life. Similarly, in another more detailed aspect of the invention, the syringe shield is magnetically attracted to the radiopharmaceutical pig. Further details of this embodiment provide for superior shielding of the radioactive material.

In yet another more detailed aspect of the invention, the radiopharmaceutical pig and/or the syringe shield can be made of tungsten, which is a metal having superior radiation shielding properties as compared to conventional lead shielding. Due to the superior shielding properties of tungsten, the radiopharmaceutical pig and the syringe shield can be made much smaller and much lighter than would otherwise be possible if they were made from lead. This size and weight reduction enables easy handling of these devices by workers, thereby reducing labor costs and the time needed for the handling of a radioactive material.

Another embodiment of the invention provides for multifunctional three-piece radiopharmaceutical pig for the transportation of a syringe containing radioactive material. This radiopharmaceutical pig has a lower piece mounted to a middle piece that is in turn mounted to an upper piece to cooperatively enclose the syringe. One advantage of this radiopharmaceutical pig is that the syringe can be discharged into the patient without removing the syringe from the middle portion of the radiopharmaceutical pig thereby avoiding radiation exposure that would otherwise occur by removing the syringe and putting it in a syringe shield. Thus, the multi-functional middle piece of the radiopharmaceutical pig can continuously shield workers from the body of the syringe for the period of after the radiopharmaceutical pig is received in the hospital until the discharge of the syringe.

Another embodiment of the invention provides a method of filling a syringe with a radioactive material from a drawing station that includes a base and a support arm for holding a radiopharmaceutical pig containing a container of radioactive material in an internal cavity closed by a cap. The method includes receiving the radiopharmaceutical pig holding the container of radioactive material and pivoting the support arm of the drawing station in at least two predetermined axes to position the radiopharmaceutical pig for filling the syringe. The radiopharmaceutical pig is mounted to the support arm of the drawing station and the cap is removed from the radiopharmaceutical pig to create an opening exposing the container of radioactive material. The needle of the syringe is then inserted into the container of radioactive material and the syringe plunger is pulled to draw radioactive material into the body of the syringe. This method provides advantages similar to the those already described herein.

Other features and advantages of the present invention will become apparent from the following description of the preferred embodiment, taken in conjunction with the accompanying drawings, which illustrate, by way of example, the principles of the invention.

BRIEF DESCRIPTION OF THE DRAWINGS

The following drawings illustrate a presently preferred embodiment of the invention, in which:

FIG. 3 is an exploded perspective view of the drawing station of FIG. 1;

FIG. 4 is a perspective view of the radiopharmaceutical pig of FIG. 1;

FIG. 5 is a side view of the PET syringe shield holding of FIG. 2;

FIG. 6 is a cross sectional view of the syringe shield of FIG. 5, taken along lines 6—6;

FIG. 7 is a side view of a PET syringe radiopharmaceutical pig;

FIG. 8 is a cross sectional view of the radiopharmaceutical pig of FIG. 7, taken along lines 8—8;

FIG. 9 is an exploded side view of the radiopharmaceutical pig of FIG. 7;

FIG. 9A is a top view of the middle piece of the radiopharmaceutical pig of FIG. 7.

DESCRIPTION OF THE PREFERRED EMBODIMENT

Figure 1:
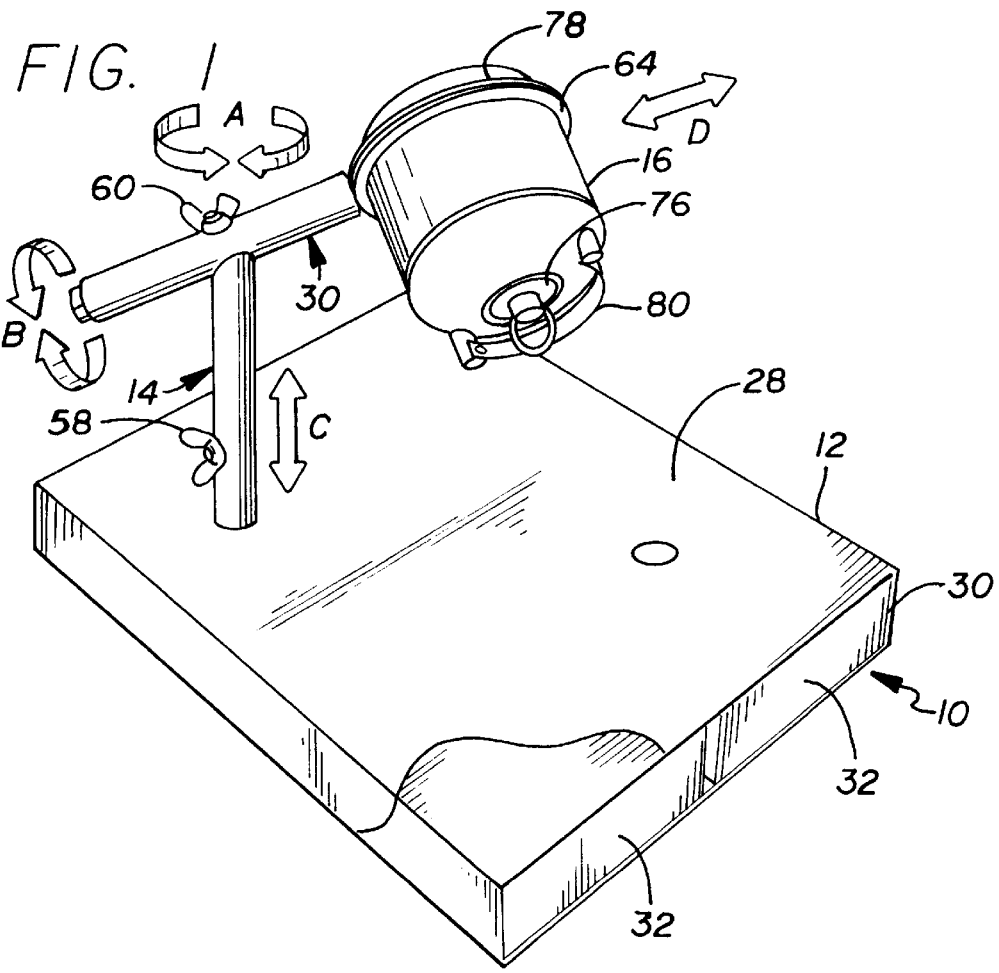
FIG. 1 is a perspective view of a preferred embodiment of a drawing station with a radiopharmaceutical pig mounted thereon.
Figure 2:
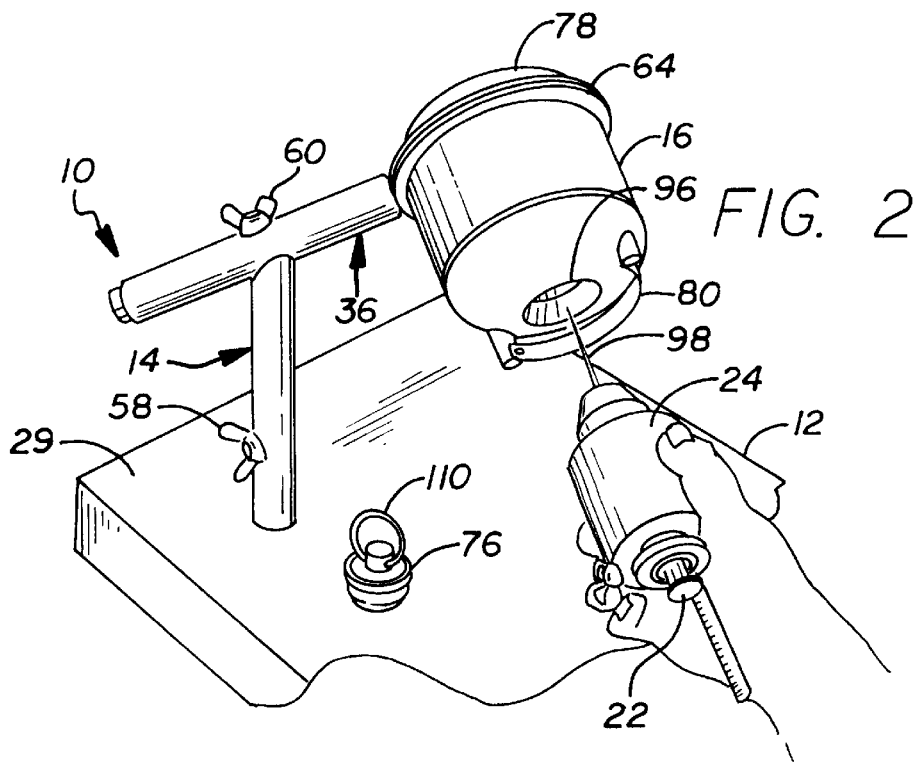
FIG. 2 is a perspective view of the drawing station of FIG. 1, showing a syringe shield holding a syringe in alignment with the drawing station.

Referring now to the drawings, and particularly to FIGS. 1–3 thereof, one embodiment of the invention is a drawing station system for use in handling highly-radioactive positron emission tomography ("PET") radiopharmaceuticals. The system includes a drawing station, generally referred to by the reference numeral 10, having a base 12 and an arm assembly 14 that holds a radiopharmaceutical pig 16 in a position for transfer of PET radiopharmaceutical 18 inside a vial 20 within the pig (see FIG. 4A) to a syringe 22 mounted within a radiation resistant syringe shield 24. The radiopharmaceutical pig is used to transport the PET material from a cyclotron to the drawing station.

The drawing station 10 advantageously allows a health care worker to easily pivot the radiopharmaceutical pig 16 about two axes A and B to position the radiopharmaceutical pig for a transfer of the PET radiopharmaceutical from the radiopharmaceutical pig to the syringe 22. The pig is also adjustable longitudinally along these axes, as indicated by arrows C and D. Further, as will be described below, the radiopharmaceutical pig has a magnetically mounted cap 26 that can be removed and replaced very quickly, thereby reducing the time in which radiation escapes from the radiopharmaceutical pig.

The radiopharmaceutical pig 16 and the syringe shield 24 are preferably made of tungsten, which is a metal having superior radiation shielding properties as compared to lead, which has long been used for the shielding of radiopharmaceuticals. Due to the superior shielding properties of tungsten, the radiopharmaceutical pig and the syringe shield are smaller and much lighter than would otherwise be possible if they were made from lead. This size and weight reduction enables easy handling by health care workers, thereby reducing labor costs and the time needed for the handling of a radiopharmaceutical. For example, because the radiopharmaceutical pig is much lighter than a conventional lead pig, health care workers can more easily place and remove the pig in the drawing station 10. Further, because the radiopharmaceutical pig is about 66% lighter and is much smaller than a conventional massive lead shield only one health care worker is required to manipulate the pig, resulting in savings and a practical increase in productivity.

The base 12 of the radiopharmaceutical pig 16 is generally rectangular and hollow. The base has an upper surface 28 and rectangular openings 30 at each end to allow the placement of lead bricks 32 inside of the base. The lead bricks act as a counterweight to prevent the drawing station 10 from tipping over under the weight of the radiopharmaceutical pig 16. The lead bricks also act as shielding to reduce the amount of radiation passing from the radiopharmaceutical pig through the base. Because the drawing station may be located on a desk or table, beneath which may be the legs of a health care worker, this extra shielding is beneficial. The base is preferably made of stainless steel or another material of suitable strength and rigidity.

As shown in FIG. 3, the arm assembly 14 includes a vertical support 34, a generally T-shaped tubular arm 36 and a ring support 38 for holding the radiopharmaceutical pig 16.

The vertical support has a threaded lower end 40 that projects through a hole 42 in the upper surface of the base 28. A nut 44 and a washer 46 located under the upper surface of the base fasten the vertical support to the base. The vertical support has a number of circumferential channels 48 along its length to enable vertical adjustment of the tubular arm 36 and the radiopharmaceutical pig 16. In particular, the tubular arm has a hollow vertical portion 50 and a hollow cross portion 52, each with a threaded set hole 54 and 56 to accept a wing nut 58 and 60. The wing nut 58 that mounts to the hole 54 in the vertical portion 50 of the tubular arm projects through this hole 54 and into one of the circumferential channels 48 in the vertical support to lock the tubular arm 36 on the vertical support 34. Before this wingnut is tightened, a health care worker can adjust the vertical and rotational position of the tubular arm to facilitate the drawing process. All of the components of the arm assembly 14 can be made of stainless steel or another materials having similar strength and rigidity.

The ring support 38 has a cylindrical body 62 mounted to a circular ring 64. The diameter of the body 62 is sized to allow the body to pass into the cross portion 52 of the support arm 36. The body 62 of the ring support has several depressions 66 to accept the end of the wingnut 60 mounted in the cross portion 52 of the support arm to limit the rotation of the ring support about its longitudinal axis (see arrows B). Thus, the position of the ring support can by adjusted along two axes and, by tightening both wingnuts, a health care worker can lock the position of the ring support before the radiopharmaceutical pig 16 is placed within the ring, as is described below. A small projection 68 is located on one end of the cross portion 52 of the support arm 36. The projection prevents the spinning of the ring support 38 by physically extending into the space through which the ring 64 must pass during its rotation. Because the ring support will not spin, it is unlikely that the radiopharmaceutical pig will flip over and fall out of the ring support 64.

Figure 4A:
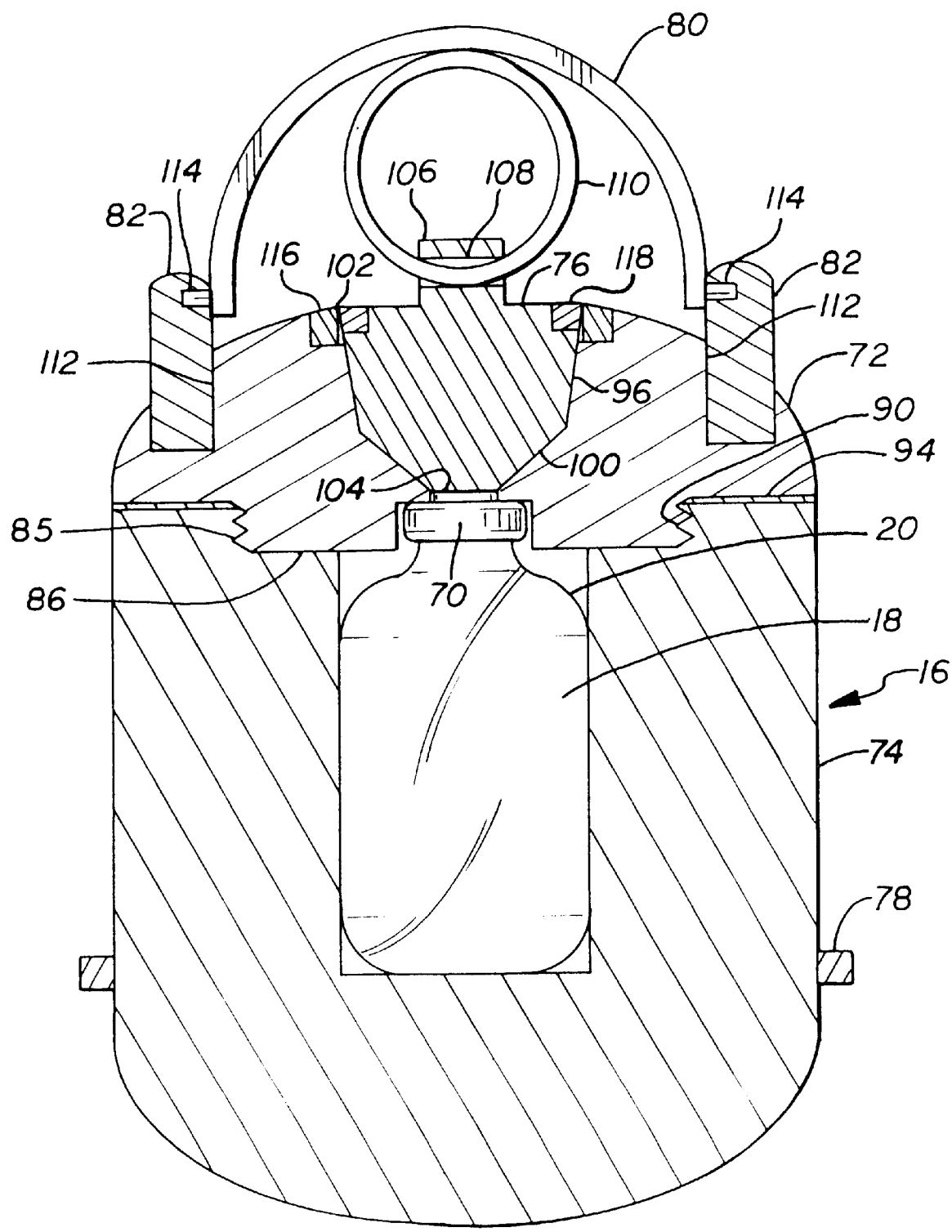
FIG. 4A is cross sectional view of the radiopharmaceutical pig of FIG. 4, taken along lines 4A—4A.

FIGS. 4 and 4A show the radiopharmaceutical pig 16, which acts as a transportation device and a dispensing device, shields the septum-capped 70 vial 20 containing a PET isotope or a PET radiopharmaceutical 18. The radiopharmaceutical pig includes an upper portion 72, a lower portion 74, a cap 76, a mounting ring 78, and a handle 80 pivoting on two posts 32. The lower portion of the radiopharmaceutical pig 74 has an exterior surface 84 upon which the mounting ring 78 is located, near to the bottom of the radiopharmaceutical pig. The outer diameter of the mounting ring is greater than the inner diameter of the ring 64 on the ring support 38. Thus, when the radiopharmaceutical pig is placed through the ring, the mounting ring of the radiopharmaceutical pig will abut the ring of the ring support. Accordingly, once the pig 16 is inverted and placed through the ring of the ring support, most of the radiopharmaceutical pig hangs through the ring, thereby enabling gravity to hold the mounting ring 78 pig securely up against the ring of the ring support.

The upper end 86 of the lower radiopharmaceutical pig portion 74 has a threaded circular depression 88 configured to accept a threaded circular projection 90 located on the lower end 92 of the upper radiopharmaceutical pig portion 72. A plastic washer 94 is located between the upper and lower radiopharmaceutical pig portions to prevent health care workers from screwing the pig portions together too tightly. The upper portion 76 of the radiopharmaceutical pig 16 has a central passageway 96 located to allow the needle 98 of the syringe 22 to penetrate the septum top 70 of the vial 18. The passageway has a smooth frustoconical portion 100 located between a first opening 102 on top of the radiopharmaceutical pig and a smaller opening 104 in the lower end 90 of the upper radiopharmaceutical pig advantageously reduce the amount of radiation that escapes upon the removal of the cap 76.

The upper tip 106 of the cap 76 has a horizontal throughhole 108 to accommodate a wire ring 110 that allows a user to grab the cap for its insertion and removal. The posts 82 are mounted in holes 112 in the upper radiopharmaceutical pig portion 72. Each post has an opposing hole 114 therein to pivotally accept the curved handle 80 therein. The posts are mounted to the upper radiopharmaceutical pig portion by welding, threads or any other suitable mechanical or adhesive fastener. The mounting ring 78 is fastened to the lower portion of the radiopharmaceutical pig in a similar manner. The cap 76 and the upper and lower portions 72 and 74 of the radiopharmaceutical pig 16 are preferably made of tungsten and are formed by well known molding techniques. However, other well known radiation-resistant materials and other well known manufacturing techniques could be used as well.

The cap 76 is held in the upper opening 102 of the radiopharmaceutical pig 16 by magnetic force. A permanently magnetic ring 46 is concentrically located around the upper opening 102 in the upper radiopharmaceutical pig portion 72. A corresponding ring preferably made of stainless steel 118 is located concentrically around the upper edge of the cap. The ring in the cap is attracted to the magnetic ring in the upper radiopharmaceutical pig, thereby advantageously holding the cap on the radiopharmaceutical pig without the need for a screw-type mechanical linkage. Because the cap can quickly be removed and replaced without any rotation or alignment of mechanical linkages, the time during which radiation escapes from the radiopharmaceutical pig is advantageously reduced. This reduction is especially significant because of the high radioactivity of PET isotopes and radiopharmaceuticals.

FIGS. 5 and 6 show the syringe shield 24 that is used to fill the syringe 22 with the material in the radiopharmaceutical pig 16 mounted in the drawing station 10. Like the radiopharmaceutical pig, the syringe shield is made from tungsten to achieve a reduction in its size and weight. The syringe shield has a tubular body 120 with a proximal end 122, a distal end 124 and a syringe volume scale 126. As is well known, the syringe held by the shield has a cylindrical body 128, the needle 98 and a plunger 130. A passageway 132 extends between openings 134 in the ends of the syringe shield. The diameter of the passageway is large enough to accept the bodies of both 3 cc. and 5 cc. syringes. However, the diameter of the passageway is less than a finger flange 136 on the end of the syringe body.

The proximal end 122 of the syringe shield 24 is frustoconically-shaped so that it can abut the frustoconical portion 100 in the upper opening 102 in the upper portion 72 of the radiopharmaceutical pig 16. A ring 138 preferably made of stainless steel and mounted concentrically around the proximal end of the syringe shield is magnetically attracted to the magnet 116 on the radiopharmaceutical pig. This ring 128 and the magnet biases the syringe shield toward the radiopharmaceutical pig to help the health care worker hold the syringe shield in the opening 102 of the radiopharmaceutical pig. The needle 98 of the syringe 22 protrudes from the proximal end of the syringe shield.

The distal end 124 of the syringe shield 24 has a threaded insert 140 to accept a threaded ring 142 thereon. The insert engages threads 141 on the inside of the passage 132. The ring 142 has a threaded central hole 144 and a threaded peripheral hole 146 to accept a screw 148 that fastens the volume scale 126 to the syringe shield. The volume scale is marked so that the amount of material in the syringe 22 can be determined without the need to view the body 128 of the syringe. Instead, the volume of the syringe can be determined by simply observing the change in position of the end of the syringe plunger 130. Because of the high radiation of PET radiopharmaceuticals and isotopes, the syringe shield does not have a window for viewing the volume of the material in the body of the syringe. Scales of different size are used for syringes 22 of different sizes.

The method of use of the drawing station system will now be described. The radiopharmaceutical pig 16 holding the vial of PET radiopharmaceutical or PET isotope arrives in the vicinity of the drawing station 10. The health care worker adjusts the position of the arm assembly 14 on the drawing station, inverts the pig and places it through the ring 64 on the ring support 38.

The health care worker then places an empty syringe 22 in the syringe shield 24. The magnetically attached cap 76 is then removed from the radiopharmaceutical pig to expose the septum cap of the vial 18 through the narrow second opening 104 in the upper portion 72 of the radiopharmaceutical pig 16. The needle 98 and the proximal end 122 of the syringe shield are moved into the opening 102 in the radiopharmaceutical pig with the magnetic attraction between the ring 138 on the shield and the magnet 116 on the radiopharmaceutical pig helping to hold the shield against the radiopharmaceutical pig. The plunger 130 of the syringe is moved back along the scale 126 of the syringe shield to draw a predetermined amount of radioactive material from the vial and into the syringe. The shield and syringe are then removed from the radiopharmaceutical pig, which is quickly recapped. The syringe is then transported and discharged using the special radiopharmaceutical pig described below.

FIGS. 7–10 illustrate a special radiopharmaceutical pig 150 for transporting the syringe 22 after is has been filled with PET isotope or PET radiopharmaceutical. This radiopharmaceutical pig 150 includes a lower piece 152, a middle piece 154, and an upper piece 156. The lower piece 152 has an external surface 158 with flat portions 160 that tend to prevent the pig from rolling if it falls over. The lower piece is formed of an inverted cone-shaped tungsten piece 159 and a corresponding section of stainless steel 161. The lower piece 152 has a threaded upper end 162 that mates with a threaded lower end 164 on the middle piece 154. The lower piece has a central cavity 166 with an opening sized 168 to accept the capped needle 98 of the syringe and located in alignment with a central passage 170 in the middle piece 152 of the radiopharmaceutical pig 150. The central passage 170 is sized to accept the body 128 of the syringe 22 therein. In turn, the upper piece of the radiopharmaceutical pig 156 has a cavity 172 with an opening 174 aligned with the central passage 170 of the middle piece of the radiopharmaceutical pig 154. The plunger 30 of the syringe fits within the cavity 172 in the upper piece of the radiopharmaceutical pig 156.

The radiopharmaceutical pig 150 has a handle 176 mounted to a ring 178 circumferentially mounted about the middle piece 154 of the radiopharmaceutical pig. The upper end 180 of the middle piece of the radiopharmaceutical pig has an oval depression 182 sized to accept the flange 136 of the syringe 22 therein to limit rotation of the syringe. The upper end of the middle piece 162 also has threads 178 to engage threads 186 on the lower end of the upper piece 156. The upper end 190 of the upper piece 156 is tapered and has a throughhole 192 to accept a rod-shaped handle 194 having two finger depressions 196 therein. A set screw 198 fastens the handle to the radiopharmaceutical pig. The radiopharmaceutical pig 150 can also be made of tungsten.

Figure 10:
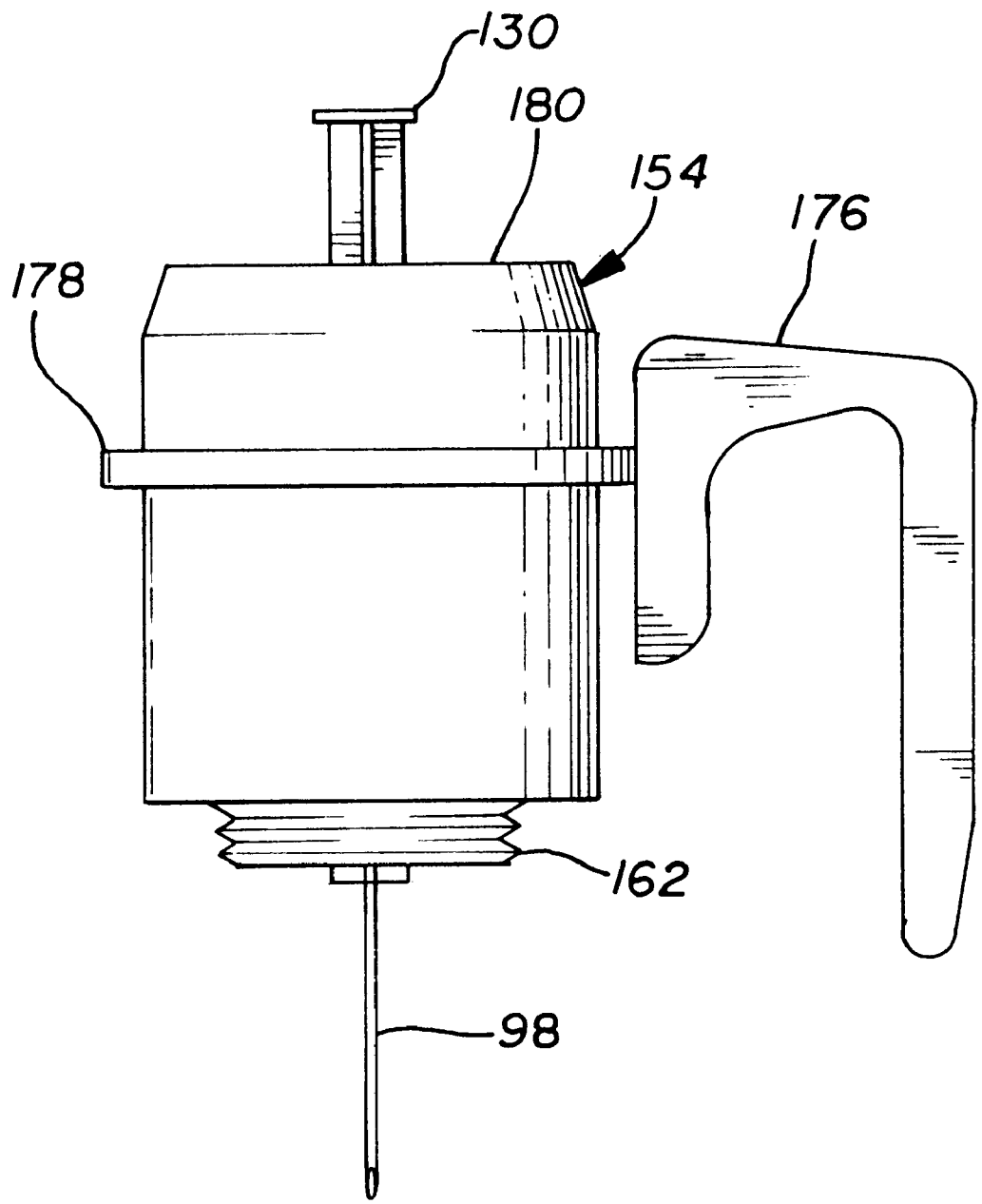
FIG. 10 is a side view of the middle piece of the radiopharmaceutical pig of FIG. 7, shown holding a syringe.

One advantage of this three-piece radiopharmaceutical pig 150 is that the syringe 22 can be discharged into the patient without removing the syringe from the middle piece 154 of the radiopharmaceutical pig. Thus, the middle piece 154 of the radiopharmaceutical pig advantageously shields workers from the body of the syringe 128 after the radiopharmaceutical pig 150 is received in the hospital. As shown in FIG. 10, a health care worker can remove the upper and lower pieces 156 and 152 of the radiopharmaceutical pig to expose the needle 98 and plunger 130 of the syringe. The needle can then be positioned for injection and the plunger can be depressed without removing the syringe from the middle shield piece.

While a particular form of the invention has been illustrated and described, it will be apparent that various modifications can be made without departing from the spirit and scope of the invention. Accordingly, it is not intended that the invention be limited, except as by the claims to be filed in this matter.

We claim:

1. A drawing station system for transferring radioactive material from a container of radioactive material to a syringe having a needle protruding from one end and a plunger protruding from the other end, the system comprising:
   a base;
   a support extending upwardly from the base;
   a first arm pivotally mounted to the support for rotation about a first predetermined axis;
   a second arm pivotally mounted to the first arm for rotation about a second predetermined axis; and
   a radiopharmaceutical pig having a cap and an interior surface defining a cavity with an opening sized to accept the cap to enclose the container of radioactive material in the cavity, the opening further positioned adjacent to the container to allow access thereto, the radiopharmaceutical pig releasably mounted to the second arm such that the radiopharmaceutical pig is pivotable about both predetermined axes upon the rotation of the first arm and the second arm, thereby positioning the container for penetration by the syringe needle to draw radioactive material from the container into the syringe.

2. The drawing station system as defined in claim 1, wherein the second arm has a ring mounted thereon and the radiopharmaceutical pig has a corresponding ring mounted around its circumference, the ring on the radiopharmaceutical pig having a diameter sized such that the ring on the radiopharmaceutical pig abuts the ring on the second arm for the mounting of the pig to the second arm.

3. The drawing station system as defined in claim 2, wherein the first arm includes a tubular first portion and a tubular second portion, the tubular first portion fitting over the support of the base and the tubular second portion extending outwardly from the tubular first portion to accept the second arm therein, the tubular second portion having an end with a projection sized to engage the ring on the second arm with an interference fit to limit the rotation of the second arm about the second axis.

4. The drawing station system as defined in claim 1, wherein the cap of the radiopharmaceutical pig is magnetically held in engagement with the radiopharmaceutical pig.

5. The drawing station system as defined in claim 4, wherein the radiopharmaceutical pig further comprises a magnetic ring mounted around the opening to the cavity.

6. The drawing station system as defined in claim 5, wherein the cap of the radiopharmaceutical pig further comprises a ring made of material that is magnetically attracted to the magnet around the opening of the pig to removably fasten the cap to the pig.

7. The drawing station system as defined in claim 5, wherein the ring on the cap of the radiopharmaceutical pig is made of ferromagnetic material.

8. The drawing station system as defined in claim 5, further comprising a syringe shield having a proximal end, a distal end and an interior surface extending therebetween to define a passage with openings in each end, the passage sized to accept the syringe therein, with the needle of the syringe projecting from the proximal end of the shield, the proximal end of the shield configured to mate with the opening in the radiopharmaceutical pig to shield the opening of the pig.

9. The drawing station system as defined in claim 8, wherein the syringe shield further comprises a material that is magnetically attracted to the magnet on the radiopharmaceutical pig.

10. The drawing station system as defined in claim 1, further comprising a syringe shield having a body with a proximal end, a distal end and an interior surface extending therebetween to define a passage with openings in each end, the passage sized to accept the syringe therein with the needle of the syringe projecting from the proximal end of the shield, the proximal end of the shield configured to mate with the opening in the radiopharmaceutical pig to shield the opening of the pig.

11. The drawing station system as defined in claim 10, wherein the body of the syringe shield comprises a continuous and uninterrupted structure without any a window therein.

12. The drawing station system as defined in claim 10, wherein the syringe shield further comprises a scale mounted adjacent to its distal end, the scale calibrated to indicate the volume of radioactive material transferred to the syringe based on the position of the end of the plunger of the syringe.

13. A radiopharmaceutical pig assembly for transporting a container of radioactive material, comprising:
   a radiation dense body;
   an interior surface within the body defining a cavity with a first opening in the body, the cavity sized to hold the container of radioactive material therein, the first opening of the cavity positioned adjacent to the container to allow access thereto;
   a radiation dense cap configured to fit across the first opening of the cavity and magnetically mounted thereto to releasible enclose the container of radioactive material therein.

14. The radiopharmaceutical pig assembly as defined in claim 13, wherein the body and cap are made of tungsten.

15. The radiopharmaceutical pig assembly as defined in claim 13, wherein the body of the pig is comprised of an upper portion releasably mated to a lower portion and wherein at least a portion of the interior surface of the body is located in the upper portion of the pig to define the first opening in the upper portion of the pig and to further define a second narrower opening adjacent to the container of radioactive material to further shield the radioactive material in the container.

16. The radiopharmaceutical pig assembly as defined in claim 15, including a frustoconical portion between the first opening and the second opening of the upper portion of the body, and wherein the cap has a corresponding frustoconical surface for mating the cap to the frustoconical portion to fit across the first and second openings.

17. The radiopharmaceutical pig assembly as defined in claim 16, wherein the cap fits across the first and second openings in the body without any rotational movement of the cap relative to the body.

18. The radiopharmaceutical pig assembly as defined in claim 13, further comprising a radiation dense syringe shield having a proximal end, a distal end and an interior surface extending therebetween to define a passage with openings in each end, the passage sized to accept a hypodermic syringe with a needle therein such that the needle of the syringe projects from the proximal end of the shield, the proximal end of the shield configured to mate with the first opening in the radiopharmaceutical pig to shield the first opening of the radiopharmaceutical pig upon the removal of the cap and the mating of the syringe shield to the first opening of the radiopharmaceutical pig.

19. The radiopharmaceutical pig assembly as defined in claim 18, wherein the syringe shield further comprises a material that is magnetically attracted to the body of the pig.

20. The radiopharmaceutical pig assembly as defined in claim 18, wherein the body of the syringe shield comprises a continuous and uninterrupted structure without any window therein.

21. The radiopharmaceutical pig assembly as defined in claim 18, wherein the syringe shield further comprises a scale mounted adjacent to its distal end, the scale calibrated to indicate the change in volume of radioactive material in the syringe.

22. The radiopharmaceutical pig assembly as defined in claim 13, wherein a magnet is mounted on the body of the pig adjacent to the opening in the pig and wherein the cap further includes a portion that is magnetically attracted to the magnet.

23. The radiopharmaceutical pig assembly as defined in claim 22, wherein the magnet is ring-shaped and is mounted around the opening on the body of the pig.

24. The radiopharmaceutical pig assembly as defined in claim 23, wherein the magnetic portion of the cap is ring-shaped.

25. A syringe shield for holding a hypodermic syringe having a needle, a plunger, and a body containing radioactive material, the shield comprising:

a radiation-resistant body with a proximal end, a distal end and an interior surface extending therebetween to define a passage with openings in each end, the passage being sized to accept the body of the hypodermic syringe therein such that the needle of the syringe projects from the proximal end of the shield and such that the plunger projects from the distal end of the shield; and a scale mounted adjacent to the distal end of the body, the scale bearing markings calibrated to indicate the change in volume of radioactive material in the syringe based on the position of the syringe plunger.

26. The syringe shield as defined claim 25, wherein the body of the syringe shield comprises a continuous and uninterrupted structure without any a window therein.

27. The syringe shield as defined in claim 25, wherein the body of the syringe shield is made of tungsten.

28. A radiopharmaceutical pig assembly for shielding a syringe containing radioactive material during transport and discharge of the syringe, the syringe having a body with a needle and an opposing plunger extending therefrom, the radiopharmaceutical pig assembly comprising:

a radiation-resistant lower body portion having an exterior surface, an upper end, and an interior surface defining a first internal cavity with an opening in the upper end sized to accept the needle of the syringe therein, the upper end of the lower body portion being threaded;

a radiation-resistant mid body portion having an exterior surface, an upper end, a lower end and an interior surface extending therebetween to define a passageway between openings in the upper and lower ends of the mid body portion, the passageway sized to accept the body of the syringe therein, the lower end of the mid body portion being threaded to releasably engage the threads on the lower body portion, the passageway in the mid body portion located in alignment with the cavity in the lower body portion upon their engagement;

a radiation-resistant upper body portion having an exterior surface, an upper end, a lower end, and an interior surface defining a second internal cavity with an opening in the lower end of the upper body portion sized to accept the plunger of the syringe therein, the lower end being threaded to releasably engage the threads on the mid body portion such that the passageway in the mid body portion is located in alignment with the cavity in the upper body portion, and a handle mounted on the mid body portion, wherein the interior surface of the mid body portion also defines a shoulder in the passageway configured to engage the body of the syringe such that the syringe body will not fall through the passageway to allow removal of the upper and lower body portions and the discharge of the syringe without the removal of the syringe from the mid body portion.

29. The radiopharmaceutical pig assembly as defined in claim 28, wherein the upper end of the upper body portion includes a T-shaped handle.

30. The radiopharmaceutical pig assembly as defined in claim 28, wherein the external surface of the lower body portion includes a plurality of flat spots to reduce rolling of the pig assembly.

31. The radiopharmaceutical pig assembly as defined in claim 28, wherein substantially all of the body portions are made of tungsten.

32. A method of filling a syringe with a radioactive material from a drawing station including a base and a support arm for holding a radiopharmaceutical pig holding a septum-capped container of radioactive material in an internal cavity closed by a cap, the syringe having a body with a needle and an opposing plunger extending from the body, the method comprising:

receiving the radiopharmaceutical pig holding the container of radioactive material;

pivoting the support arm of the drawing station in at least two predetermined axes to position the radiopharmaceutical pig for filling the syringe;

mounting the radiopharmaceutical pig to the support arm of the drawing station;

removing the cap from the radiopharmaceutical pig to create an opening exposing the container of radioactive material;

inserting the needle of the syringe into the container of radioactive material; and pulling the plunger of the syringe to draw radioactive material into the body of the syringe.

33. The method of filling a syringe with a radioactive material as defined in claim 32, wherein the body of the syringe is inside a radiation resistant shield and the inserting of the needle of the syringe into the container of radioactive material comprises:

aligning the exposed needle of the syringe with the opening in the radiopharmaceutical pig;

moving the syringe and the shield to mate with the opening, thereby penetrating the container with the syringe needle; and applying a magnetic force to bias the syringe shield toward the radiopharmaceutical pig while the syringe shield is mated with the opening of the radiopharmaceutical pig.

* * * * *